United States Patent [19]

Waldstreicher

[11] Patent Number: 5,512,555
[45] Date of Patent: Apr. 30, 1996

[54] METHOD OF TREATING SWEAT-RELATED CONDITIONS USING FINASTERIDE, EPRISTERIDE AND A CHOLESTAN-3-ONE

[75] Inventor: Joanne Waldstreicher, Scotch Plains, N.J.

[73] Assignee: Merck & Co., Inc., Rahway, N.J.

[21] Appl. No.: 278,434

[22] Filed: Jul. 21, 1994

[51] Int. Cl.$^6$ .................... A61K 31/59; A61K 31/44; A61K 7/34

[52] U.S. Cl. .................... 514/168; 514/284; 514/176; 424/65; 424/69

[58] Field of Search .................... 514/167, 176, 514/284; 424/69, 65

[56] References Cited

U.S. PATENT DOCUMENTS 4,760,071  7/1988  Rasmusson et al. .................... 514/284

FOREIGN PATENT DOCUMENTS

WO93/23419  11/1993  WIPO.

OTHER PUBLICATIONS

Takayasu et al. "Activity of Testosterone 5alpha-reductase in Various Tissues of Human Skin" J. Invest. Dermatol., vol. 74, pp. 187–191 (1980).

Mortimer et al. "A double-blind controlled cross-over trial of cyrpoterone acetate in females with hidradenitis suppurativa" British J. Dermatology, vol. 115, pp. 263–268 (1986).

Sawers et al. "Control of hidradenitis suppurativa in women using combined antiandrogen(cyproterone acetate) and oestrogen therapy" British J. Dermatology, vol. 115, pp. 269–274 (1986).

Harris, et al. "Identification and selective inhibition of an isozyme of steroid 5 alpha reductase in human scalp" Proc. Natl. Acad. Sci., vol. 89, pp. 10787–10792 (1992).

Primary Examiner—Theodore J. Criares
Attorney, Agent, or Firm—Catherine D. Fitch; Carol S. Quagliato

[57] ABSTRACT

The instant invention involves methods of treating sweat related conditions with compounds that are 5α-reductase inhibitors. The 5α-reductase inhibitors may be administered alone or in combination with other active agents to treat conditions such as apocrine gland sweating, hyperhidrosis, and hydradenitis suppurativa.

14 Claims, No Drawings

METHOD OF TREATING SWEAT-RELATED CONDITIONS USING FINASTERIDE, EPRISTERIDE AND A CHOLESTAN-3-ONE

The present invention is concerned with the treatment of sweat-related conditions with compounds that are 5α-reductase inhibitors.

BACKGROUND OF THE INVENTION

Apocrine sweat glands, comprised of ducts that open directly into the hair follicle, are largely confined to regions of the axilla and perineum (genital-anal area) and become functional just before puberty. Although this suggests that gonadal steroids (i.e. androgens and estrogens) play a role in their development, the exact hormones have not been identified.

In man, the role of the apocrine gland is unclear, since the eccrine sweat glands (which open directly onto the surface of the skin and which are distributed over nearly the entire body surface) perform the thermoregulatory function. The odor, which results from bacterial action on aprocrine sweat, may have had a role in man in the past, but is now clearly vestigial. Sweat collected from the surface of the skin is contaminated by sebum (since there is a common opening to the surface of the skin), secretions from eccrine sweat glands, as well as bacteria. Based on animal data, it is thought that aprocrine sweat contains protein, nitrogen, potassium, sodium, calcium, magnesium, chloride, bicarbonate and lactate. Sweat is secreted in a pulsatile manner, presumably due to synchronous contraction of myoepithelial cells across the body.

Unlike eccrine glands which are under cholinergic control, apocrine gland secretion is largely under adrenergic control. Both local and circulating epinephrine and norepinephrine can stimulate secretion. Emotional stimuli, after puberty, are strong inducers of secretion. Drugs that affect the adrenergic system (such as reserpine) affect apocrine gland secretion. 5α-Reductase levels are very high in apocrine glands. Therefore, activity of this enzyme is believed to play a role in controlling secretion. However, a 5α-reductase inhibitor has not been previously studied as an inhibitor of apocrine secretion.

Hyperhidrosis is defined as an increase above normal in sweat production. This is diagnosed when sweating occurs under conditions where it would not normally be expected or is excessive in response to emotional or thermal stimuli.

Localized hyperhidrosis of the axilla is most likely due to a combination of increased eccrine and apocrine sweat production. This disorder is usually most problematic when there is both an increased ambient temperature and emotional stimulation. Axillary sweating, unlike eccrine sweating, is largely resistant to most common antiperspirant regimens. Aluminum salts or anticholinergic agents produce only a 50% decrease in armpit sweating, but nearly a 100% decrease in eccrine sweating elsewhere. However, Shelley described a regimen of aluminum chloride in absolute ethanol or isopropyl alcohol under occlusive plastic wrap at bedtime which more effectively inhibits axillary sweat. Other reported treatments are sympathectomy of the fifth thoracic ganglion, local excision of affected axillary skin, cryosurgery, tranquilizers and anticholinergic agents.

Hydradenitis suppurativa (HS) is a chronic inflammatory disorder of apocrine sweat glands in which abscesses and drainage sinuses develop in the axilla and/or perineal area. The pathogenesis of HS is felt to be similar to acne: poral occlusion, bacterial colonization, androgenic stimulation and inflammation all seem to be important. Although its etiology is multifactorial, it is likely that a change in any one of the four etiologic factors will have a significant impact on the course of the disease. Antibiotics (affecting bacterial colonization) and isotretinoin (ACCUTANE®) (affecting the keratinous plugging of the sweat duct) are used to treat this disorder. Antiandrogens such as cyproterone (not available in the U.S.) and estrogen have also been used to control HS.

The enzyme 5α-reductase converts testosterone ("T") to dihydrotestosterone in certain target organs as well as in the circulating blood serum. It is known that inhibitors of 5α-reductase will serve to prevent or lessen symptoms of hyperandrogenic stimulation such as acne vulgaris, seborrhea, female hirsutism, androgenic alopecia, and benign prostatic hyperplasia. See especially U.S. Pat. Nos. 4,377,584 and 4,760,07 1, both assigned to Merck & Co., Inc. It is also now known that two isozymes of 560-reductase exist: isozyme type 2 which principally interacts within prostatic tissues, and isozyme type 1, discovered more recently, which principally interacts within skin tissues. See, e.g., G. Hams, et al., *Proc. Natl. ACad. Sci. USA*, vol. 89, pp. 10787–10791 (November 1992).

Since androgens are felt to play a role in the pubertal onset of aprocrine gland function and the pathogenesis of HS and there is a large amount of 5α-reductase activity in apocrine sweat glands, apocrine sweat gland production should be decreased by 5α-reductase inhibitors, such as finasteride (marketed in the U.S. under the tradename PROSCAR® for the treatment of benign prostatic hyperplasia) and 4,7β-dimethyl-4-aza-5α-cholestan-3-one (also known as MK-386). A decrease in sweat production, should be observed with either oral administration or topical application of 5α-reductase inhibitors to the axillae or perineum. Therefore, these agents will be useful as antiperspirants and for the treatment of other androgenmediated conditions related to sweat glands, such as local hyperhidrosis and HS.

SUMMARY OF THE INVENTION

The instant invention involves a novel method of treating sweat-related conditions, such as apocrine gland sweating, also known as perspiration, hyperhidrosis and HS comprising the administration of a therapeutically effective amount of a 5α-reductase inhibitor. Also provided are pharmaceutical compositions comprising a pharmaceutically acceptable carrier, a 5α-reductase inhibitor and additional active agents such as aluminum hydroxide, anticholinergic agents, antibiotics, and isotretinoin which are useful for the treatment of sweat-related conditions.

DETAILED DESCRIPTION OF THE INVENTION

The present invention has the objective of providing methods of treating sweat-related conditions including apocrine gland sweating, hyperhidrosis and hydradenitis suppurativa (HS) by oral, systemic, parenteral or topical administration of a 5α-reductase inhibitor or a combination of 5α-reductase inhibitors, either alone or in combination with other active agents such as aluminum hydroxide, anticholinergic agents, antibiotics and isotretinoin.

The term "5α-reductase inhibitor" as used herein is intended to include compounds which are active as inhibitors of either or both of the isozymes of 5α-reductase, such as, e.g., inhibitors of 5α-reductase type 1, such as e.g., 4,715-dimethyl-4-aza-5α-cholestan-3-one (also known as MK-386; as disclosed in WO 93/23420 to Merck & Co. Inc.), inhibitors of 5α-reductase type 2, such as e.g., finasteride, epristeride (also known as SKF-105657, SmithKline Beecham), ONO-3805 (Ono Pharmaceutical Co., Ltd.), FK-143 (Fujisawa), and TZP-4238 (Teikokuzoki), and those which are active as dual inhibitors of both isozymes type 1 and 2, such as e.g., those disclosed in WO 94/00121 and WO94/00125 to SmithKline Beecham. Also encompassed by the instant method invention is the use of a combination of an inhibitor of 5α-reductase type 1 with an inhibitor of 5α-reductase type 2, such as e.g., the use of a combination of finasteride with MK-386. Many compounds which are 5α-reductase inhibitors have been described in the art; compounds which are 5α-reductase inhibitors can also be determined by the 5α-reductase assay further described below.

Examples of compounds specifically and generically which are 5α-reductase inhibitors and the use of which are encompassed within the present invention, include, but are not limited to, those described in the following patents and publications: U.S. Pat. Nos. 4,377,584; 4,760,071; 4,845,104; 4,859,681; 5,049,562; 5,120,742; 5,138,063; and 5,151,429; and WO 93/23038, WO 93/23039, WO 93/23040, WO 93/23041, WO 93/23048, WO 93/23050, WO 93/23051, WO 93/234 19, WO 93/23420, WO 93/16996, WO 93/23042, WO 94/00121, WO 94/00125, WO 94/03474, WO 94/03475, WO 94/03476, WO 94/07909, WO 93/13124, U.S. Pat. No. 5,302,528, EP 532,190, EP 291,245. The above list is not intended to be exhaustive, and there are many other publications which describe inhibitors of 5α-reductase.

The term "therapeutically effective amount" means that amount of a drug or pharmaceutical agent that will elicit the biological or medical response of a tissue, system, animal or human that is being sought by a researcher, veterinarian, medical doctor or their clinician. The novel methods of treatment of this invention are for conditions known to those skilled in the art. In fact, apocrine gland sweating, or perspiration, is a condition commonly known and understood by average consumers who lack any specialized medical skills.

In particular, with regard to treating the disorders of hyperhidrosis and hydradenitis suppurativa, the term "therapeutically effective amount" is intended to mean that amount of a 50α-reductase inhibitor or combination of inhibitors that will prevent or alleviate the symptoms of the disorder. With regard to treating the condition of aprocrine gland sweating, i.e., for use of a 5α-reductase inhibitor or combination of inhibitors as an anti-perspirant, the term "therapeutically effective amount" is intended to mean that amount of inhibitor that will prevent or reduce the amount of apocrine gland secretions.

The present invention also has the objective of providing suitable topical, oral, systemic and parenteral pharmaceutical s formulations for use in the novel methods of treatment of the present invention. The compositions containing 5α-reductase inhibitor compounds as the active ingredient for use in the treatment of the above-noted conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

The daily dosage of the compounds may be varied over a range from 0.01 to 1,000 mg per adult human/per day. For oral administration, the compositions are preferably provided in the form of tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0002 mg./kg. to about 50 mg./kg. of body weight per day. The range is more particularly from about 0.001 mg./kg. to 7 mg./kg. of body weight per day.

Advantageously, compounds of the present invention may be administered in a single daily dose, or the total daily dosage may be administered in divided doses of two, three or four times daily. Furthermore, compounds for the present invention can be administered in intranasal form via use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For the treatment of sweat-related conditions, the compounds of the present invention may be administered in a pharmaceutical composition comprising the active compound in combination with a pharmaceutically acceptable carrier adapted for topical administration. Topical pharmaceutical compositions may be, e.g., in the form of a solution, cream, ointment, gel, lotion, or aerosol formulation adapted for application to the skin. These topical pharmaceutical compositions containing the compounds of the present invention ordinarily include about 0.005% to 5% by weight of the active compound in admixture with a pharmaceutically acceptable vehicle.

For the treatment of apocrine gland sweating and hyperhidrosis, the 5α-reductase inhibitor compounds can be used in combination with a therapeutically effective amount of a topical antiperspirant such as an aluminum salt, e.g. aluminum hydroxide and/or a topical or oral anti-cholinergic agent and optionally including a deodorant. For the treatment of HS, the 5α-reductase inhibitor compounds can be used in combination with an anticholinergic agent, antibiotics and/or isotretinoin each of which can be administered topically or orally. Where combination treatment is employed, the active agents may be administered in a single pharmaceutical dosage formulation. Alternatively, a combined therapy can be employed wherein the active agents are administered in separate dosage formulations. For example, a 5α-reductase inhibitor and aluminum hydroxide can be administered in a single topical dosage formulation, or each active agent can be administered in a separate dosage formulation, e.g., an oral dosage formulation of the 5α-reductase inhibitor in combination with a topical dosage formulation of aluminum hydroxide. See, e.g., U.S. Pat. Nos. 4,377,584 and 4,760,071 which describe dosages and formulations for 5α-reductase inhibitors.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carders (collectively referred to herein as "carder" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allanloin, glycerine, vitamin A and E oils, mineral oil, PPG2 myristyl propionate, and the like, to form, e.g., alcoholic solutions, topical cleansers, cleansing creams, skin gels, skin lotions, aerosol or non-aerosol sprays, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

EXAMPLE 1

BIOLOGICAL ASSAYS

Preparation of Human prostatic and scalp 5α-reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1.500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-reductase assay

The reaction mixture for the type 1 5α-reductase contained 40 mM potassium phosphate, pH 6.5, 5 mM [7-$^3$H]-testosterone, 1 mM dithiothreitol and 500 μM NADPH in a final volume of 100 μl. The reaction mixture for the type 2 5α-reductase contained 40 mM sodium citrate, pH 5.5, 0.3 mM [7-$^3$H]-testosterone, 1 mM dithiothreitol and 500 μM NADPH in a final volume of 100 μl. Typically, the assay was initiated by the addition of 50–100 μg prostatic homogenate or 75–200 μg scalp homogenate and incubated at 37° C. After 10–50 min. the reaction was quenched by extraction with 250 μl of a mixture of 70% cyclohexane: 30% ethyl acetate containing 10 μg each DHT and T. The aqueous and organic layers were separated by centrifugation at 14,000 rpm in an Eppendorf microfuge. The organic layer w, as subjected to normal phase HPLC (10 cm Whatman partisil 5 silica column equilibrated in 1 ml/min 70% cyclohexane: 30% ethyl acetate; retention times: DHT, 6.8–7.2 min.; androstanediol, 7.6–8.0 min.; T, 9.1–9.7 min.). The HPLC system consisted of a Waters Model 680 Gradient System equipped with a Hitachi Model 655αautosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Inhibition studies

Compounds were dissolved in 100% ethanol. The compound to be tested was pre-incubated with the enzyme (either 5α-reductase type 1 or 2) prior to initiation by addition of substrate testosterone. $IC_{50}$ values represent the concentration of inhibitor required to decrease enzyme conversion of testosterone to dihydrotestosterone by 50% of the control. $IC_{50}$ values were determined using a 6 point titration where the concentration of the inhibitor was varied from 0.1 to 1000 nM.

A compound referred to herein as a 5α-reductase 2 inhibitor is a compound that shows inhibition of the 5α-reductase 2 isozyme in the above-described assay, having an $IC_{50}$ value of about or under 100 nM.

A compound referred to herein as a 5α-reductase type 1 inhibitor is a compound that shows inhibition of the 5α-reductase type 1 isozyme in the above-described assay, having an $IC_{50}$ value of about or under 100 nM.

A compound referred to herein as a dual 5α-reductase type 1 and 2 inhibitor is a compound that shows inhibition of both the type 1 and type 2 isozymes, having an $IC_{50}$ value of about or under 100 nM for each isozyme.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the s mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A pharmaceutical composition comprising
  (a) a pharmaceutically acceptable carrier,
  (b) a therapeutically effective amount of a 5α-reductase inhibitor selected from finasteride, epristeride or 4,7β-dimethyl-4-aza-5α-cholestan-3-one, and
  (c) a therapeutically effective amount of an antiperspirant.

2. A composition of claim 1 wherein the antiperspirant is an aluminum salt.

3. A composition of claim 2 wherein the aluminum salt is aluminum hydroxide.

4. A pharmaceutical composition comprising
  (a) a pharmaceutically acceptable carrier,
  (b) a therapeutically effective amount of the 5α-reductase type 1 inhibitor, 4,7β-dimethyl-4-aza-5α-cholestan-3-one and a 5α-reductase type 2 inhibitor selected from finasteride and epristeride, or
  (c) a therapeutically effective amount of an antiperspirant.

5. A method of treating a condition selected from apocrine gland sweating, hyperhidrosis, or hydradenitis suppurativa comprising adminstering to a person in need of such treatment a therapeutically effective amount of a 5α-reductase inhibitor selected from finasteride, epristeride or 4,7β-dimethyl-4-aza-5α-cholestan-3-one.

6. The method of claim 5 wherein the inhibitor is a 5α-reductase type 2 inhibitor selected from finasteride or epristeride.

7. The method of claim 6 wherein the inhibitor is finasteride.

8. The method of claim 5 wherein the inhibitor is the 5α-reductase type 1 inhibitor, 4,7β-dimethyl-4-aza-5α-cholestan-3-one.

9. The method of claim 6 further comprising the administration of the 5α-reductase type 1 inhibitor, 4,7β-dimethyl-4-aza-5α-cholestan-3-one.

10. The method of claim 9 wherein the 5α-reductase type 2 inhibitor is finasteride.

11. The method of claim 5 wherein the condition is apocrine gland sweating, and further comprising administration of a therapeutically effective amount of aluminum hydroxide.

12. The method of claim 5 wherein the condition is hyperhidrosis, and further comprising administration of a therapeutically effective amount of aluminum hydroxide.

13. The method of claim 5 wherein the 5α-reductase inhibitor is administered orally.

14. The method of claim 5 wherein the 5α-reductase inhibitor is administered topically.

\* \* \* \* \*

UNITED STATES PATENT AND TRADEMARK OFFICE
CERTIFICATE OF CORRECTION

PATENT NO. : 5,512,555

DATED : 4/30/96

INVENTOR(S) : JOANNE WALDSTREICHER

It is certified that error appears in the above-identified patent and that said Letters Patent is hereby corrected as shown below:

In Claim 4, at Column 8, line 4, delete "finasteride and epristeride, or" and insert therefor -- finasteride or epristeride, and -- .

In Claim 5, at Column 8, line 8, delete "adminstering" and insert therefor -- administering --.

Signed and Sealed this

Thirtieth Day of July, 1996

Attest:

BRUCE LEHMAN

Attesting Officer

Commissioner of Patents and Trademarks